United States Patent

Rizzi et al.

Patent Number: 5,128,468
Date of Patent: Jul. 7, 1992

[54] PROCESS FOR PREPARING 2-ARYL-3-HYDROXY-CIS-2,3-DIHYDRO-1,5-BENZOTHIAZEPIN-4(5H)-ONES AND THEIR DERIVATIVES

[75] Inventors: Amleto Rizzi, Alte Ceccato; Gaetano Marchioro, Vicenza, both of Italy

[73] Assignee: FIS—Fabbrica Italiana Sintetici S.p.A., Italy

[21] Appl. No.: 615,687

[22] Filed: Nov. 19, 1990

[30] Foreign Application Priority Data

Nov. 23, 1989 [IT] Italy .................. 22497 A/89

[51] Int. Cl.⁵ .......................... C07D 306/13
[52] U.S. Cl. ................................ 540/491
[58] Field of Search ........................ 540/491

[56] References Cited

U.S. PATENT DOCUMENTS

| | | | |
|---|---|---|---|
| 4,590,188 | 3/1986 | Takeda et al. | 540/491 |
| 5,008,411 | 4/1991 | Coffen et al. | 540/491 |
| 5,008,433 | 1/1991 | Palmer | 540/491 |

Primary Examiner—Robert T. Bond
Attorney, Agent, or Firm—Diller, Ramik & Wight

[57] ABSTRACT

The present invention relates to a novel process for synthetizing 2-aryl-3-hydroxy-cis-2,3-dihydro-1,5-benzothiazepin-4-(5H)-ones and their derivaives, as optically pure compounds or as their racemic mixtures, having the following general formula (I):

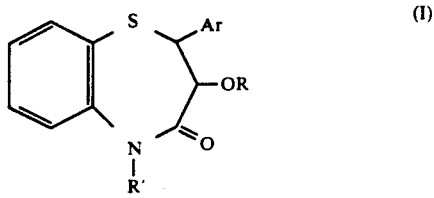

by using, as synthesis precursors, methyl esters of 2-hydroxy-3-arylthio-3-arylpropionic acids in their threo form, as their hydrochlorides, or as free bases, of generally formula (II):

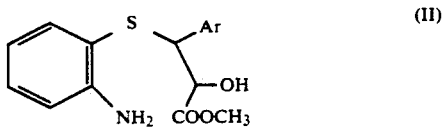

and treating such precursors with an excess of sodium methoxide, at low temperature, in diethyleneglycol, dimethylether, diemthylformamide and ethyl acetate.

8 Claims, No Drawings

PROCESS FOR PREPARING 2-ARYL-3-HYDROXY-CIS-2,3-DIHYDRO-1,5-BENZOTHIAZEPIN-4(5H)-ONES AND THEIR DERIVATIVES

The present invention relates to a novel process for synthetizing 1,5-benzothiazepinic derivatives known as important intermediates, and as drugs endowed with excellent psychoneurotic, coronary vasodilating and calcium-blocking activities.

In particular, the method according to the present invention is a method of synthesis for preparing derivatives of 1,5-benzothiazepine, having the general formula (I):

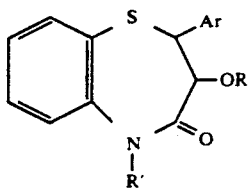

wherein:
Ar represents a lower-alkoxy-substituted phenyl,
R represents a hydrogen atom, an acetyl or a lower ω-carboxyalkyl group, and
R' represents a hydrogen atom, a lower alkyl or an lower alkyl group substituted in its ω-position, such as 2-chloroethyl, 2-dimethylaminoethyl, 3-bromopropyl.

In the following disclosure, by the term "lower alkyl" is meant, an alkoxy group which contains from 1 to 4 carbon atoms (such as, e.g., methyl, ethyl, n-propyl, isopropyl, n-butyl, isobutyl and tert.-butyl); and by the term "lower alkoxy", is meant, an alkoxy group which contains from 1 to 4 carbon atoms (such as, e.g., methoxy, ethoxy, n-propoxy, isopropoxy, n-butoxy, isobutoxy and tert.-butoxy).

It is known to prepare compounds of formula (I). See, e.g., Jpn Tokkio Koho 7843,517 (1978), Tanabe Seyaku; Jpn Kohai Tokkyo Koho JP 57136,581 (1982), Nippon Kayaku. It is also known that it is difficult to resolve and isolate the optically active acids from which compound of formula (I) can be prepared. Furthermore, as already reported by E. Decorte and F. Moimas, Italian patent No. 1,175,112, obtaining such optically active acids by means of the acidification of a solution of their chiral base salts, involves a considerable loss of materials and the formation of secondary products.

According to the present invention, compounds corresponding to general formula (I) are prepared by cyclizing the lower alkyl esters of the corresponding threo-diarylhydroxy-propionic acids having the formula (II):

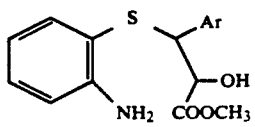

by treating such precursors with a lower alkoxide of an alkali metal an aprotic polar solvent; or mixtures thereof. According to the instant invention, such a cyclising process is particularly advantageous because of its high yields, and because, by taking place at low temperatures, it avoids problems of formation of by-products, and prevents undesired reactions from taking place.

Furthermore, the process according to the present invention can be applied to esters of general formula (II), both as optically pure compounds, and in the form of their racemic mixture, it being possible to select whether a possibly desired separation of the enantiomers should be carried out before or after the cyclizing reaction.

On the other hand, this cyclizing reaction can be applied also to the hydrochlorides of the starting ester compounds, such as, e.g., methyl (+)-threo-2-hydroxy-3-(2'-aminophenylthio)-3-(4''-methoxyphenyl)-propionate hydrochloride, which is a key intermediate after the resolution of the relevant enantiomers.

According to a further embodiment of the invention, the alkylation of the amidic nitrogen can be carried out in the same reaction mixture, so as to provide a "one-pot" process for obtaining useful intermediates for the synthesis of interesting compounds for the pharmaceutical sector.

In that way, derivatives of 1,5-benzothiazepine substituted in their 5-position can be obtained, such as, e.g., (+)-2-(4'-methoxyphenyl)-3-hydroxy-5-[2-(dimethylamino)-ethyl]-cis-2,3-dihydro-1,5-benzothiazepin-4(5H)-one hydrochloride, by starting from the hydrochloride adduct of the relevant ester of formula (II), directly and with good yields, with the cyclizing and the alkylation being carried out in one single reaction step.

The compounds of general formula (II), which can be easily obtained by treating, at a high temperature, in the presence of hydrogen chloride gas, in the corresponding alcohol, as disclosed in applicant's co-pending patent application Ser. No. 07/615,686, filed Nov. 19, 1990, are stable, well-crystallizing substances which can be easily dried, and which make it possible for the corresponding optically active acid to be recovered to an extent of more than 95%.

Accordingly to the present invention, esters of formula (II), as hydrochlorides or as free bases, yield the corresponding 1,5-benzothiazepine with a yield higher than 90% upon treatment with from 1 to 5 equivalents of sodium methoxide, at a temperature of 0° C. at maximum, for example, in the range of from −20° to 0° C., in such solvents as dimethylformamide, diethyleneglycol, dimethylether, ethyl acetate, triethylamine or acetone. Accordingly to a further embodiment of the present invention, compounds of general formula (I) in which R' represents an alkyl chain or an ω-substituted alkyl chain, such as, e.g., 2-(dimethylamino)-ethyl, can be obtained by means of the simple addition of the correspoding alkyl halide to the reaction mixture. According to the latter embodiment, the process can be also advantageously be accomplished into two steps, wherein the first step comprises isolating the 1,5-benzothiazepinic derivative, in which R' is equivalent to hydrogen, and the second step involves the treatment with an alkali metal alkoxide and the corresponding halide.

In that way, compounds falling within the scope of general formula (I) can be obtained; and, among them, e.g., a very important drug in the management of cardiacal diseases, whose generic name is "diltiazem" [Ar=4-methoxyphenyl, R=COCH₃, R'=CH₂CH₂—N(CH₃)₂]. The process of the present invention enables the preparation of compounds of formula (I) on a large industrial scale, in particular when compared to methods relying on the use of riskful reactants, such as sodium hydride in dimethylsulfoxide, as reported in U.S. Pat. No. 3,562,257, or based on the use of reactants unsuitable for the scaling-up to the industrial level, such as anhydrous silica gel, as proposed by U.S. Pat. No. 4,416,819.

The fact that according to the instant invention the cyclizing is carried out at low temperatures makes it possible an optimal conversion, in terms of quality and yield, to be obtained from the first optically active intermediate to the 1,5-benzothiazepine with an already predetermined configuration of both chiral centers in C(2) and C(3).

According to a particular, important practical embodiment of the present invention, a process is used, which is characterized in that it comprises the following steps:

(a) resolution of the racemic mixture of the acid corresponding to said compound of formula (II) into its optical antipodes by means of the salification thereof with cyclohexylamine, according to the reaction:

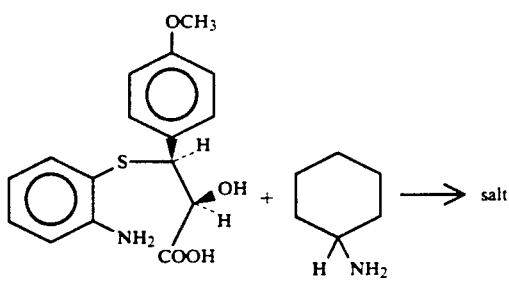

and crystallization of the so-formed enantiomeric salts;

(b) reaction of the (+)-enantiomeric salt separated from the enantiomeric salts formed in the above step (a) with hydrogen chloride gas to form the hydrochloride of the (+)-salt of said compound of formula (II):

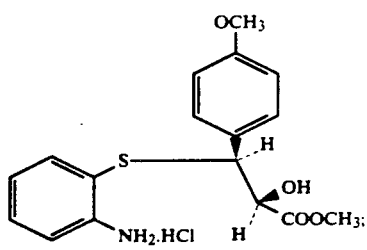

(c) reaction of said hydrochloride of the salt of said compound of formula (II) formed in said step (b) with the methoxide of an alkali metal to form the (+)-enantiomer of said compound of formula (I) in which R'=H.

The following Examples and preparations illustrate the experimental conditions and techniques of the present invention, without limiting the invention in any way.

EXAMPLE 1

Cis-2-(4'-methoxyphenyl)-3-hydroxy-2,3-dihydro-1,5-benzothiazepin-4(5H)-one

Under a nitrogen blanketing stream, 7.0 g (130 mmol) of sodium methoxide is poured in 150 ml of diethyleneglycol dimethylether (diglyme) at the temperature of 0° C. The mixture is cooled down to −10° C., then 33.3 g (100 mmol) of methyl threo-2-hydroxy-3-(2'-aminophenylthio)-3-(4''-methoxyphenyl)-propionate is added. When addition is complete, the temperature is allowed to slowly increase. The reaction is allowed to proceed at room temperature for a 1-hour reaction time, then the reaction mixture is poured in 600 ml of ice-water mixture.

The precipitate is filtered off, is washed with water and is dried. 28.1 g of product is obtained.

Yield 93%.

Melting point 172°-173° C.

EXAMPLE 2

Cis-2-(4'-methoxyphenyl)-3-acetoxy-2,3-dihydro-1,5-benzothiazepin-4(5H)-one

A mixture of 6.5 g (120 mmol) of sodium methoxide in 100 ml of acetone and 50 ml of triethylamine is prepared at −10° C. under a nitrogen blanketing atmosphere. To this mixture, 33.3 g (100 mmol) of methyl threo-2-hydroxy-3-(2'-aminophenylthio)-3-(4''-methoxyphenyl)-propionate is added and then the temperature is allowed to slowly increase up to about 20° C. and the mixture is allowed to react at that temperature for a 2-hour reaction time.

The temperature is then increased up to 0° C., 6 ml of acetic acid and then 30 ml of acetic anhydride are added dropwise and the reaction mixture is allowed to react overnight at room temperature.

The reaction mixture is poured in 900 ml of ice-water mixture, the whole mixture is filtered, and the filter cake is washed with a little water; the so obtained precipitate is treated at boiling temperature with 100 ml of methanol, then is filtered; 26.3 g of dry product is obtained.

Yield 76%.

Melting point 200°-202° C.

EXAMPLE 3

Cis-(+)-2-(4'-methoxyphenyl)-3-hydroxy-2,3-dihydro-1,5-benzothiazepin-4(5H)-one

A mixture of 12.0 g (22.2 mmol) of sodium methoxide in 150 ml of dimethylformamide is formed under a nitrogen stream, and the whole mixture is then cooled to the temperature of −10° C.

With cooling, so that during the addition the temperature never exceeds −5° C., 37.0 g (100 mmol) of methyl (+)-threo-2-hydroxy-3-(2'-aminophenylthio)-3-(4''-methoxyphenyl)-propionate hydrochloride is incrementally added.

When the addition is complete, the temperature is allowed to increase up to 10° C., the reaction is allowed to proceed under such conditions for a further 30 minutes, and the reaction mixture is subsequently poured in a solution of 600 ml of ice-water mixture, containing 6 ml of acetic acid.

The precipitate obtained is filtered off, is washed with water and methanol, then is dried.

28.4 g of a white, crystalline solid is obtained.

Yield 94%.

Melting point 200°–202° C.

EXAMPLE 4

Cis-(+)-2-(4'-methoxyphenyl)-3-hydroxy-5-[2-(dimethylamino)-ethyl]-2,3-dihydro-1,5-benzothiazepin-4(5H)-one hydrochloride A mixture of 13.5 g (250 mmol) of sodium methoxide in 120 ml of dimethylformamide is formed under a slow nitrogen stream, and said mixture is then cooled to the temperature of −10° C.

With the temperature being always kept at values lower than −5° C., 37.0 g (100 mmol) of methyl (+)-threo-2-hydroxy-3-(2'-aminophenylthio)-3-(4''-methoxyphenyl)-propionate hydrochloride is incrementally added to this mixture.

A mixture of 26.0 g (180 mmol) of 2-chlorodimethylaminoethane hydrochloride, 50 ml of an aqueous solution of 15% of sodium hydroxide and 40 ml of isopropyl ether is separately prepared.

The organic phase is removed, and the aqueous phase is extracted again with isopropyl ether; the organic phases are combined with each other and the ethereal solution is thoroughly dried with sodium sulfate.

All of the ethereal solution is added at about 0° C. to the reaction mixture, the temperature is increased up to 65° C. and the reaction is allowed to proceed 1 hour under these conditions. The whole reaction mixture is poured in a solution of ice and water, and the resulting mass is extracted with dichloromethane.

The solvent is evaporated off and the residue is subsequently dissolved in ethanol and is acidified at low temperature with a solution at 10% of hydrogen chloride in ethanol.

A precipitate is obtained, which is filtered and dried to give 29.2 g of product.

Yield 71%.

Melting point 225°–227° C. (with decomposition)

EXAMPLE 5

Cis-2-(4'-methoxyphenyl)-3-hydroxy-2,3-dihydro-1,5-benzothiazepin-4(5H)-one

Under a nitrogen stream, 6.5 g (120 mmol) of sodium methoxide is added to 200 ml of ethyl acetate at 0° C., then the so obtained mixture is cooled to −10° C.

33.3 g (100 mmol) of methyl threo-2-hydroxy-3-(2'-aminophenylthio)-3-(4''-methoxyphenyl)-propionate is added.

The reaction mixture is left standing 1 hour at 10° C., then 7 ml of acetic acid and 50 ml of water are added, and the mixture is increased up to 60° C.

The aqueous phase is separated, 100 ml of ethyl acetate is distilled off, then the reaction mixture is allowed to crystallize by cooling.

22.9 g of product is obtained.

Yield 76%.

Melting point 174°–175° C.

EXAMPLE 6

Cis-(+)-2-(4'-methoxyphenyl)-3-hydroxy-5-[2-(dimethylaminoethyl]-2,3-dihydro-1,5-benzothiazepin-4(5H)-one hydrochloride 7.00 g (130 mmol) of sodium methoxide is added at room temperature and under a nitrogen stream, to a mixture composed by 30.1 g (100 mmol) of cis-(+)-2-(4'-methoxyphenyl)-3-hydroxy-2,3-dihydro-1,5-benzothiazepin-4(5H)-one in 120 ml of dimethylformamide.

The temperature of the solution is then increased up to 65° C.

A mixture composed by 21.6 g (150 mmol) of 2-chlorodimethylaminoethane hydrochloride, 40 ml of isopropyl ether and 40 ml of an aqueous solution of 15% of sodium hydroxide is separately prepared. The organic phase is removed, and the aqueous phase is extracted again with isopropyl ether; the organic phases are combined with each other and the ethereal solution is thoroughly dried over sodium sulfate.

This solution is then dropwise added to the reaction mixture at 65° C., then the reaction mixture is kept with stirring for a further 30 minutes after addition completion. The whole mass is poured in a water-ice mixture and is extracted with dichloromethane.

After the evaporation of the solvent, the residue is dissolved in ethanol and is acidified at low temperature with a solution at 10% of hydrogen chloride in ethanol.

A white, crystalline solid is obtained, whose dry weight is of 32.8 g.

Yield 80%.

Melting point 225°–227° C. (with decomposition).

EXAMPLE 7

Cis-(+)-2-(4'-methoxyphenyl)-3-hydroxy-5-[2-(dimethylamino)-ethyl]-2,3-dihydro-1,5-benzothiazepin-4(5H)-one hydrochloride A mixture of 21.6 g (400 mmol) of sodium methoxide in 150 ml of dimethylformamide is prepared under a nitrogen stream, then is cooled down to −10° C.

To this mixture, 37.0 g (100 mmol) of methyl (+)-threo-2-hydroxy-3-(2'-aminophenylthio)-3-(4''-methoxyphenyl)-propionate hydrochloride is incrementally added, with the temperature being always kept at a value lower than −5° C.

When addition is complete, the temperature is allowed to slowly increase up to 10° C., then 18.7 g (130 mmol) of 2-chloro-dimethylaminoethane hydrochloride is added.

The temperature is then allowed to rise up to 65° C., the reaction is allowed to proceed for 1-hour time, then the whole reaction mixture is poured in 300 ml of water-ice mixture containing 20 ml of an aqueous solution of concentrated hydrochloric acid.

The solution is filtered, alkalified and extracted with dichloromethane, then the organic phase is evaporated to dryness.

The residue is dissolved in ethanol, then a solution at 10% of hydrogen chloride in ethanol is added in order to adjust the pH value at about 3 at low temperature.

A precipitate is obtained, which is filtered and dried, giving 24.6 of product.

Yield 60%.

Melting point 225°–227° C. (with decomposition).

SYNTHESIS OF COMPOUNDS OF FORMULA (II)

PREPARATION 1

Methyl threo-2-hydroxy-3-(2'-aminophenylthio)-3-(4''-methoxyphenyl)-propionate 208 g (1.00 mol) of trans-methyl-3-(4'-methoxyphenyl)-glycidate is dissolved in 1,500 ml of toluene under a nitrogen atmosphere.

The reaction mixture is heated up to its refluxing temperature and 118 ml (138 g, 1.10 mol) of 2-aminothiophenol is added dropwise to it.

When addition is complete, the reaction mixture is kept under refluxing conditions for 1 further hour, then is allowed to crystallized by cooling. The obtained product is recrystallized from 900 ml of ethanol. An amount of 237 g (dry weight) of a soft solid of white colour is obtained.

Yield 71%.

Melting point 90°-92° C.

PREPARATION 2

Methyl (+)-threo-2-hydroxy-3-(2'-aminophenylthio)-3-(4''-methoxyphenyl)-propionate hydrochloride 169 g (384 mmol) of (+)-phenylethylamine salt of (+)-threo-2-hydroxy-3-(2'-aminophenylthio)-3-(4''-methoxyphenyl)-propionic acid, with $[\alpha]_D^{23} = +370°$ (c=0.510, ethanol) is dissolved in 400 ml of methanol.

Hydrogen chloride gas is bubbled through the solution, the solution is heated to its boiling temperature, with the addition of gas being continued, and is maintained at boiling temperature.

When precipitation begins, the flow of hydrogen chloride is discontinued, the mixture is kept refluxing for a further hour, then 200 ml of methanol is distilled off.

The reaction mixture is cooled and after filtration and drying, 135 g of a crystalline white-coloured solid is obtained.

Yield 95%.

Melting point 196°-198° C.

$[\alpha]_D^{20} = 34.9$ (c=0.635, methanol).

We claim:

1. Process for preparing 2-aryl-3-hydroxy-cis-2,3-dihydro-1,5-benzothiazepin-4(5H)-ones and their derivatives having the formula (I):

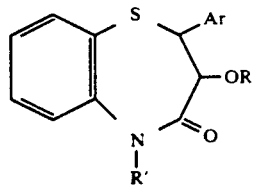

wherein:
Ar represents a lower-alkoxy-substituted phenyl,
R represents a hydrogen atom, an acetyl or a lower ω-carboxyalkyl group, and
R' represents a hydrogen atom, a lower alkyl or an ω-substituted lower alkyl group,
characterized in that it comprises the step of causing a compound of formula (II)

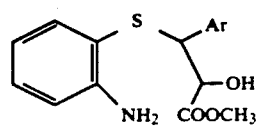

or the hydrochloride thereof, in which Ar has the above specified meaning, to react with a lower alkoxide of an alkali metal, in an aprotic polar solvent.

2. Process according to claim 1, characterized in that the reaction temperature is of 0° C. at maximum.

3. Process according to claim 1, in which in said formula (I) R' is a lower alkyl or an ω-substituted lower alkyl group, characterized in that it comprises the further step of adding to the reaction mixture the corresponding alkyl halide R'X, wherein X=halide.

4. Process according to claim 1, characterized in that said solvent is selected from the group consisting of dimethylformamide, diethyleneglycol, dimethylether, ethyl acetate, triethylamine and acetone.

5. Process according to claim 2, characterized in that said reaction temperature is in the range of from −20° C. to 0° C.

6. Process according to claim 1, characterized in that said compound of formula (II) is in optically pure form.

7. Process according to claim 6, characterized in that it comprises the following steps:

(a) resolution of the racemic mixture of the acid corresponding to said compound of formula (II) into its optical antipodes by means of a salification with cyclohexylamine, according to the reaction:

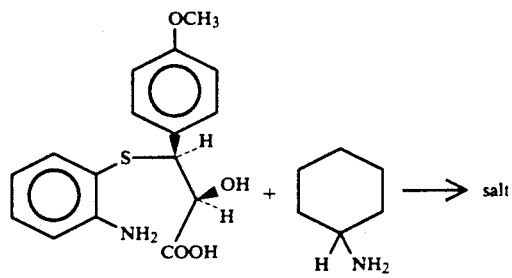

and crystallization of the so-formed enantiomeric salts;

(b) reaction of the (+) enantiomeric salt separated in (a) with hydrogen chloride gas, with the hydrochloride of the (+) salt of said compound of formula (II):

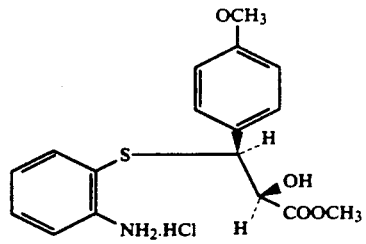

being formed; and (c) reaction of said hydrochloride of the salt of said compound of formula (II) formed in said step (b) with the methoxide of an alkali metal, with the (+) enantiomer of said compound of formula (I) in which R'=H being formed.

8. Process according to claim 7 for preparing diltiazem:

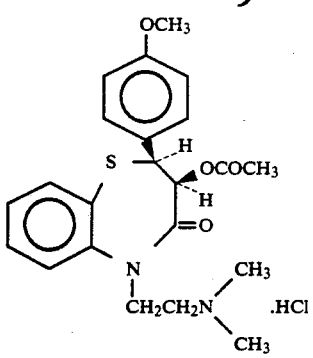
characterized in that it comprises the further step (d) of causing the (+) enantiomer formed in said step (c) with an alkyl halide
$(CH_3)_2NCH_2CH_2X$
followed by the acetylation and isolation of the corresponding hydrochloride.
* * * * *